US009757251B2

(12) United States Patent
Kim et al.

(10) Patent No.: US 9,757,251 B2
(45) Date of Patent: Sep. 12, 2017

(54) MINIMALLY INVASIVE INTERVERTEBRAL BODY RETAINING CAGE INSERTION DEVICE

(71) Applicant: MEDRICS CO., LTD., Seoul (KR)

(72) Inventors: Hyeon Seong Kim, Seoul (KR); Jeong Hwa Kim, Gwangju (KR); Hong Won Yoon, Yongin-si (KR)

(73) Assignee: MEDRICS CO., LTD., Seoul (KR)

( * ) Notice: Subject to any disclaimer, the term of this patent is extended or adjusted under 35 U.S.C. 154(b) by 0 days.

(21) Appl. No.: 15/126,901

(22) PCT Filed: Jan. 23, 2015

(86) PCT No.: PCT/KR2015/000702
§ 371 (c)(1),
(2) Date: Sep. 16, 2016

(87) PCT Pub. No.: WO2015/141940
PCT Pub. Date: Sep. 24, 2015

(65) Prior Publication Data
US 2017/0086988 A1    Mar. 30, 2017

(30) Foreign Application Priority Data
Mar. 17, 2014  (KR) ........................ 10-2014-0031246

(51) Int. Cl.
*A61F 2/44*   (2006.01)
*A61F 2/46*   (2006.01)
*A61F 2/30*   (2006.01)

(52) U.S. Cl.
CPC .......... *A61F 2/4611* (2013.01); *A61F 2/4465* (2013.01); *A61F 2002/30828* (2013.01); *A61F 2002/4475* (2013.01)

(58) Field of Classification Search
CPC .................. A61F 2/4611; A61F 2/4465; A61F 2002/30828; A61F 2002/4475;
(Continued)

(56) References Cited

U.S. PATENT DOCUMENTS 6,530,929 B1 *  3/2003  Justis ............... A61B 17/00234
                                                    606/103
7,951,153 B2 *  5/2011  Abdou .................. A61F 2/4611
                                                    606/86 A
(Continued)

FOREIGN PATENT DOCUMENTS

KR    10-2007-0117013 A    12/2007
KR    10-2010-0108299 A    10/2010
KR       10-1196784 B1     11/2012

*Primary Examiner* — Pedro Philogene
(74) *Attorney, Agent, or Firm* — Novick, Kim & Lee, PLLC; Jae Youn Kim

(57) ABSTRACT

A minimally invasive intervertebral body retaining cage insertion device is a cage insertion device for inserting a cage between adjacent vertebrae by using a screw driver for inserting a spine-retaining pedicle screw as a shaft. The intervertebral body retaining cage insertion device for a minimal invasive surgery includes: a retaining unit detachably coupled to a predetermined position on the screw driver; a position adjustment unit having holes defined along a longitudinal direction of a body and in which the retaining unit is fixed and coupled to a predetermined position of a hole; an instrument insertion guide rotatably coupled to an end of the position adjustment unit and inserted between the adjacent vertebrae; and a first cage insertion unit which moves along a rail formed on the instrument insertion guide and inserts a first cage between the adjacent vertebrae, wherein a minimally invasive operation is conducted by slightly incising the back side in a diagonal direction, it is unnecessary to rotate the direction of a cage, after inserting the same, towards the abdominal side of the human body, (Continued)

and the screw driver for inserting a spine-retaining pedicle screw (screw spike) is used as a shaft, therefore requiring no separate installation device.

11 Claims, 13 Drawing Sheets

(58) Field of Classification Search
CPC ...... A61F 2002/4658; A61F 2002/4662; A61F 2002/4666; A61F 2002/4687; A61B 17/7065; A61B 17/7077; A61B 17/7062; A61B 2017/0256; A61B 2019/461; A61B 2019/462; A61B 2019/464
USPC ...... 606/86 A, 100, 102, 103, 104, 246–279, 606/87, 96, 97, 99, 148, 130; 242/157 R; 223/99
See application file for complete search history.

(56) References Cited

U.S. PATENT DOCUMENTS

| | | | | |
|---|---|---|---|---|
| 8,974,461 B2* | 3/2015 | Abdou | ................ | A61F 2/4611 |
| | | | | 606/249 |
| 9,005,205 B2* | 4/2015 | Black | ................ | A61B 17/7004 |
| | | | | 606/86 A |
| 9,402,659 B2* | 8/2016 | McBride | ............ | A61B 17/7077 |

* cited by examiner

MINIMALLY INVASIVE INTERVERTEBRAL BODY RETAINING CAGE INSERTION DEVICE

TECHNICAL FIELD

The present invention relates to a minimally invasive intervertebral body retaining cage insertion device, and more particularly, to an intervertebral body retaining cage insertion device for a minimal invasive surgery in which a cage that substitutes for a damaged disc between intervertebral bodies is inserted between the intervertebral bodies.

BACKGROUND ART

A disc is disposed between vertebrae. Also, the outside of the disc is protected by tough fibers, and vertebral pulp exists inside the disc.

Discs function as joints and play very important roles for minimizing an impact applied to vertebrae while vertebral pulp changes in position and shape according to movement of the vertebrae. The vertebral pulp is mostly moisture (water). When we get older, an amount of moisture gradually decreases, and thus, a buffer function of a disc is lost. As a result, when an excessive pressure is applied to the fibers, backache may occur. Here, if the excessive pressure is continuously applied, the fibers may be seriously stretched or ruptured to push nerve roots placed at a rear side thereof, thereby causing pains of pelvis, legs, and the like. Thereafter, a distance between the vertebrae gradually decreases, or the vertebrae are collapsed to cause various kinds of side effects such as vertebral deformation.

There is a method, in which an intervertebral fusion device, so-called, a cage is inserted between two adjacent vertebrae after a disc between the damaged vertebrae is removed, as a method for treating diseases involved due to the disc. That is, the cage recovers the distance between the vertebrae to its original distance between the two adjacent vertebrae, which corresponds to an original height of the disc, thereby recovering the vertebral function.

The surgical method in which the cage is inserted between the vertebrae includes an anterior lumbar interbody fusion (ALIF) method in which a cage is inserted from a front side of a vertebra after an abdominal operation, a lateral lumber interbody fusion (LLIF) method in which a cage is inserted through a side portion, a transforaminal lumbar interbody fusion (TLIF) method in which a cage is inserted in a diagonal direction at a point that is spaced a distance of 30 mm to 40 mm laterally from a center of a back side, and a posterior lumbar interbody fusion (PLIF) method in which a cage is inserted from a back side.

According to the conventional TLIF surgical procedure, one side surface of the cage is inserted and located between the vertebrae in the diagonal direction through the back of the human body, and then, a front surface of the inserted cage is disposed to face the abdomen of the human body, thereby completing the insertion of the cage. An impactor that is an assisting mechanism for allowing the front surface of the cage to face the abdomen of the human body is needed. Here, force is applied to the other surface of the cage by using the impactor to rotate the cage so that the cage faces the abdomen of the human body.

In case of the conventional TLIF surgical procedure, the position of the cage is easily influenced by the skill level of an operator, and it is difficult to accurately locate the cage between the vertebrae. Thus, when the cage is not accurately located between the vertebrae, surgical operation effects may be deteriorated.

DISCLOSURE OF THE INVENTION

Technical Problem

To solve the technical problems according to the related art, an objective of the present invention is to provide an intervertebral body retaining cage insertion device for a minimal invasive surgery, in which it is unnecessary to rotate a cage so that the cage faces an abdomen of the human body after inserting the cage because a skin of the back is slightly incised in a diagonal direction to conduct the minimal invasive surgery.

Also, an objective of the present invention is to provide an intervertebral body retaining cage insertion device for a minimal invasive surgery, in which a separate installation device is unnecessary by using a screw driver for inserting a spine-retaining pedicle screw as a shaft.

Also, an objective of the present invention is to provide an intervertebral body retaining cage insertion device for a minimal invasive surgery, in which bones that are different in position from person to person are adjusted and corrected in position within the device so that a cage is accurately inserted between vertebrae.

Also, an objective of the present invention is to provide an intervertebral body retaining cage insertion device for a minimal invasive surgery, in which a cage is inserted along a rail having an arc-type curved shape to prevent neural stems of spinal nerves from being damaged when the cage is inserted.

Technical Solution

To achieve the objectives of the present invention, an intervertebral body retaining cage insertion device for a minimal invasive surgery, which inserts a cage between adjacent vertebrae by using a screw driver for inserting a spine-retaining pedicle screw as a shaft, includes: a retaining unit detachably coupled to a predetermined position on the screw driver; a position adjustment unit having a hole defined along a longitudinal direction of a body and in which the retaining unit is fixed and coupled to a predetermined position of the hole; an instrument insertion guide rotatably coupled to an end of the position adjustment unit and inserted between the adjacent vertebrae; and a first cage insertion unit moved along a rail provided on the instrument insertion guide to insert a first cage between the adjacent vertebrae.

Also, the retaining unit may include: a body; a first pressing/retaining plate disposed on one side of the body; a second pressing/retaining plate disposed to face the first pressing/retaining plate and moved to the first pressing/retaining plate to press the screw driver; a transfer screw moving the second pressing/retaining plate forward and backward; a first fastener rotating the transfer screw; and a second fastener fixed and coupled to a predetermined position of the hole defined in the position adjustment unit.

Also, the position adjustment unit may have a guide hole defined along the longitudinal direction of the body and a coupling hole to which the instrument insertion guide is coupled and include a rotation prevention protrusion preventing the instrument insertion guide from being rotated after the instrument insertion guide coupled to the coupling hole is rotated to be inserted between the adjacent vertebrae.

Also, the instrument insertion guide may include: a rotation member having one end coupled to the position adjustment unit; and a guide rail body disposed on the other end of the rotation member and provided with a rail to which the first cage insertion unit is slidably coupled.

Also, each of the guide rail body and the first cage insertion unit may have an arc-type curved shape.

Also, the first cage insertion unit may include: a body provided with a rail slidably coupled to the rail provided on the instrument insertion guide; a first cage coupling part including two pieces constituted by one side piece and the other side piece on one end of the body and coupled to the first cage; a coupling rod provided in the body, slidable forward and backward, and slid forward and inserted between the one side piece and the other side piece to support the one side piece and the other side piece in directions opposite to each other; and a rod moving member sliding the coupling rod forward and backward.

Also, the intervertebral body retaining cage insertion device may further include a spacing unit moved along the rail provided on the instrument insertion guide to space the instrument insertion guide from the first cage insertion unit so as to secure a space for inserting a second cage after the first cage insertion unit is inserted between the adjacent vertebrae.

Also, the spacing unit may include: a body provided with a rail slidably coupled to the rail provided on the instrument insertion guide; and a head part disposed on one end of the body to push and space the first cage insertion unit from the instrument insertion guide while the body is slid along the rail of the instrument insertion guide.

Also, the intervertebral body retaining cage insertion device may further include a second cage insertion unit moved between the instrument insertion guide and the first cage insertion unit along a rail provided on the first cage insertion unit to insert the second cage into the adjacent vertebrae after the first cage insertion unit is spaced apart from the instrument insertion guide by the spacing unit.

Also, each of the spacing unit and the second cage insertion unit may have an arc-type curved shape.

Also, the second cage insertion unit may include: a body provided with a rail slidably coupled to the rail provided on the first cage insertion unit; a second cage coupling part including two pieces constituted by one side piece and the other side piece on one end of the body and coupled to the second cage; a coupling rod provided in the body, slidable forward and backward, and slid forward and inserted between the one side piece and the other side piece to support the one side piece and the other side piece in directions opposite to each other; and a rod moving member sliding the coupling rod forward and backward.

Advantageous Effects

According to the intervertebral body retaining cage insertion device for the minimal invasive surgery, the skin of the back may be slightly incised in the diagonal direction to conduct the minimal invasive surgery, and also, after the cage is inserted, it may be unnecessary to rotate the cage so that the cage faces the abdomen of the human body.

Also, since the screw driver for inserting the spine-retaining pedicle screw is used as the shaft, it may be unnecessary to provide the separate installation device.

Also, since the bones that are different in position from person to person are adjusted and corrected in position within the device, the cage may be inserted into the accurate position.

Also, since the cage is inserted along the rail having the arc-type curved shape, the cage may be inserted without damaging the neural stems of the spinal nerves.

Also, after the cage is inserted along the rail having the arc-type curved shape, the cage may easily move forward by using the spacing unit. In addition, since the other cage is inserted along the rail having the arc-type curved shape, the two cages may be inserted into the accurate position between the vertebrae, and the cage that is inserted later may be coupled to be engaged with the cage that is inserted first to stably support the vertebrae without separating the two cages from each other.

MODE FOR CARRYING OUT THE INVENTION

Hereinafter, preferred embodiments of the present invention will be described in more detail with reference to the accompanying drawings.

Figure 1:
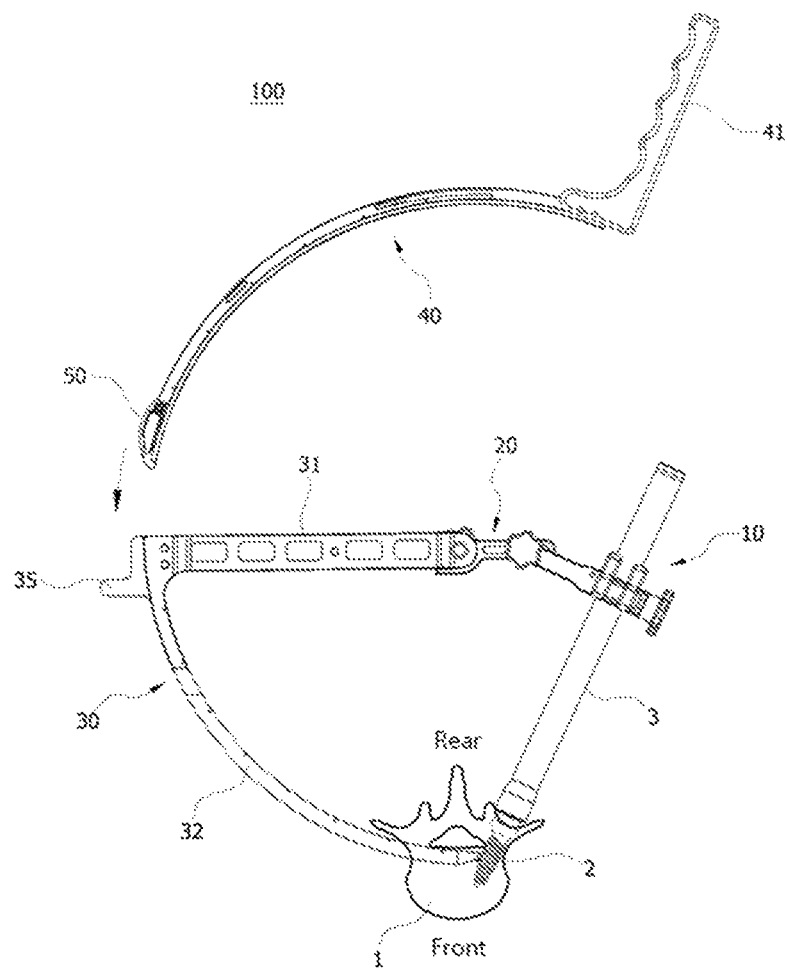
FIG. 1 is a front view illustrating a state in which an intervertebral body retaining cage insertion device for a minimal invasive surgery is coupled to a screw driver according to the present invention.
Figure 2:
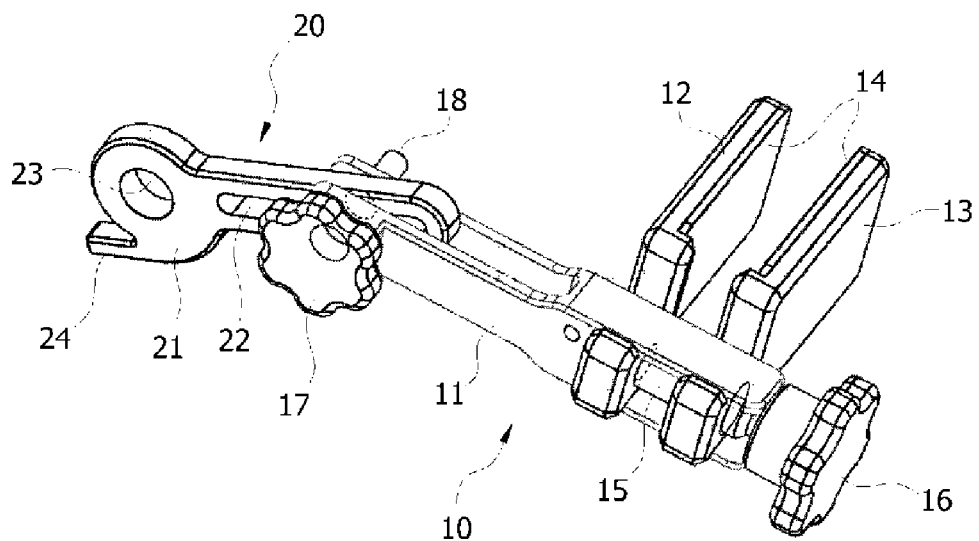
FIG. 2 is a perspective view illustrating a state in which a retaining unit and a position adjustment unit, which constitute the intervertebral body retaining cage insertion device for the minimal invasive surgery, are coupled to each other according to the present invention.
Figure 3A:
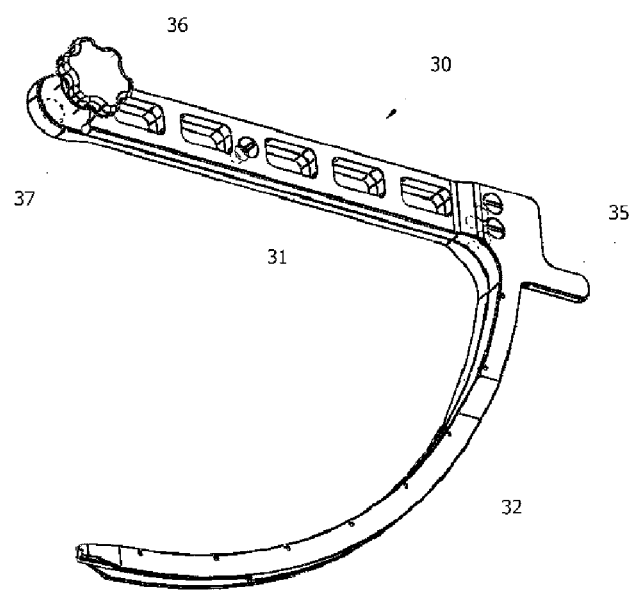
FIG. 3A is a perspective view of an instrument insertion guide constituting the intervertebral body retaining cage insertion device for the minimal invasive surgery according to the present invention.
Figure 3B:
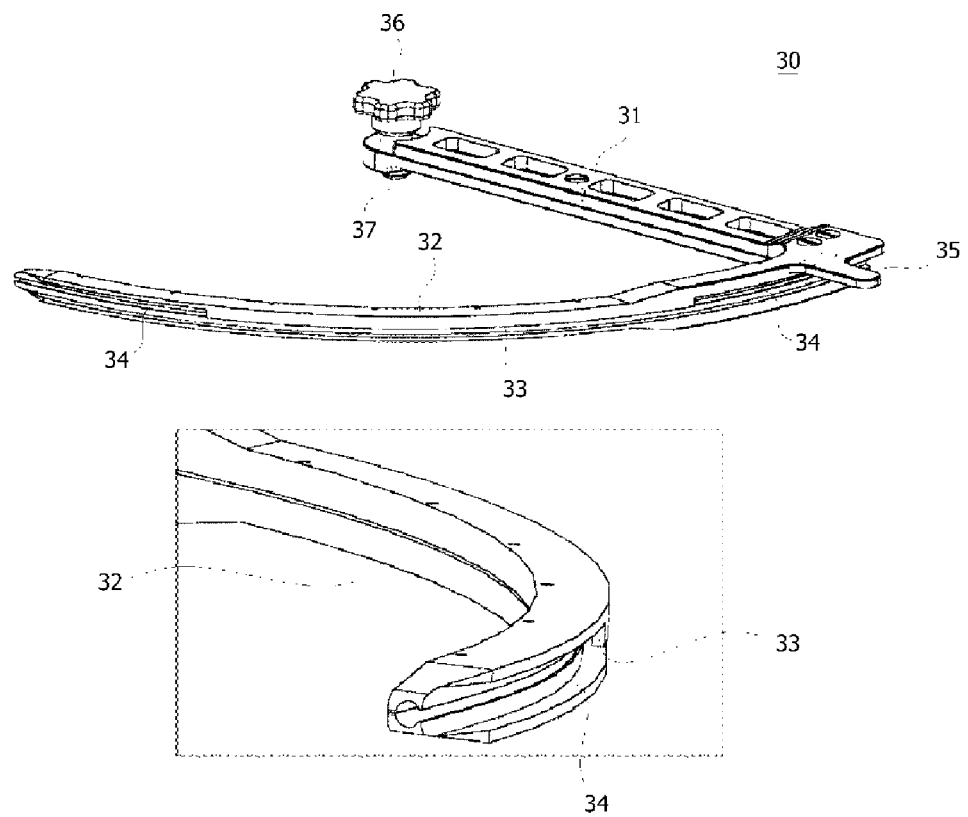
FIG. 3B is perspective and partial enlarged views of the instrument insertion guide constituting the intervertebral body retaining cage insertion device for the minimal invasive surgery according to the present invention.

Referring to FIGS. 1 to 3B, an intervertebral body retaining cage insertion device 100 for a minimal invasive surgery may be a cage insertion device for inserting a cage between adjacent vertebrae by using a screw driver 3 for inserting a spine-retaining pedicle screw 2 into a vertebra 1 as a shaft. In FIG. 1, a rear side represents the back of the human body, and a front side represents the abdomen.

A pedicle screw 2 may be a screw spike. The pedicle screw 2 is used for stably retaining the vertebrae after treating sites of lesion by connecting the vertebrae to each other through a connection rod (not shown) after implanted into the vertebrae.

The screw driver 2 is used for inserting the pedicle screw 2. The screw driver 3 coupled to the pedicle screw 2 after the pedicle screw 2 is inserted is illustrated.

The intervertebral body retaining cage insertion device 100 for the minimal invasive surgery may include a retaining unit 10, a position adjustment unit 20, an instrument insertion guide 30, and a first cage insertion unit 40 and further include a spacing unit 60 and a second cage insertion unit 70.

The retaining unit 10 is detachably coupled to the screw driver 3 at a predetermined position.

Particularly, the retaining unit 10 includes a body 11, a first pressing/retaining plate 12 disposed on one side of the body 11, a second pressing/retaining plate 13 disposed to face the first pressing/retaining plate 12 and moved to the first pressing/retaining plate 12 to press the screw driver 3, a transfer screw 15 moving the second pressing/retaining plate 13 forward and backward, a first fastener 16 rotating the transfer screw 15, and a second fastener 17 fixed and coupled to a predetermined position of a hole 22 defined in the position adjustment unit 20.

The first pressing/retaining plate 12 is fixedly installed, and a pad 14 is attached to a surface facing the second pressing/retaining plate 13 so that the first pressing/retaining plate 12 is firmly retained without being slid when being pressed and retained to the screw driver 3.

The second pressing/retaining plate 13 is moved forward and backward along a rotation direction of the transfer screw 15 to apply a pressure to the screw driver 3 or to be spaced apart from the screw driver 3. A pad 14 is attached to a surface facing the first pressing/retaining plate 12.

The transfer screw 15 is rotated by manipulating the first fastener 16 by an operator.

A groove is defined in a portion of the screw driver 3, at which the first pressing/retaining plate 12 and the second pressing/retaining plate 13 are in contact with each other. Thus, the first pressing/retaining plate 12 and the second pressing/retaining plate 13 are stably coupled to each other without being slid downward on the screw driver 3.

Also, the operator may determine whether the screw driver 3 is positioned at a center, a left side, or a right side of a rectangular portion of the pad 14 of each of the first pressing/retaining plate 12 and the second pressing/retaining plate 13. The intervertebral body retaining cage insertion device 100 for the minimal invasive surgery may be gradually moved to a direction of the head or legs of the human body through the position determination. As a result, the cage may be accurately inserted between the vertebrae in consideration of sizes and thicknesses of the vertebrae 1, which are different from person to person.

A screw part 18 may be attached to the second fastener 17, and the second fastener 17 may be coupled to the guide hole 22 defined in the position adjustment unit 20 through the screw part 18.

The hole 22 is defined in the position adjustment unit 20 along a longitudinal direction of the body 21, and the position adjustment unit 20 is retained to through the second fastener 17 after the screw part 18 of the retaining unit 10 is disposed at a predetermined position of the hole 22.

Particularly, the position adjustment unit 20 has the guide hole 22 defined in the longitudinal direction of the body 21 and a coupling hole 23 to which the instrument insertion guide 30 is coupled and includes a rotation prevention protrusion 24 preventing the instrument insertion guide 30 from being rotated after the instrument insertion guide 30 coupled to the coupling hole 23 is rotated to be inserted between the adjacent vertebrae. When being retained by using the second fastener 17, the coupling hole 23 to which the instrument insertion guide 30 is coupled may be disposed at a center of a rear side of the vertebra 1 so that the instrument insertion guide 30 is accurately inserted into a central portion between the vertebrae when the instrument insertion guide 30 is rotated. The rotation prevention protrusion 24 supports the instrument insertion guide 30 to prevent the instrument insertion guide 30 from being further rotated after the instrument insertion guide 30 is rotated and inserted between the vertebrae.

The instrument insertion guide 30 is rotatably coupled to one end of the position adjustment unit 20 and inserted between the adjacent vertebrae.

Particularly, the instrument insertion guide 30 includes a rotation member 31 having one end coupled to the coupling hole 23 of the position adjustment unit 20 and a guide rail body 32 disposed on the other end of the rotation member 31 and provided with a rail to which the first cage insertion unit 40 is slidably coupled and further includes a handle 35 disposed on one end of the guide rail body 32 so that the operator grips and rotates the handle 35. A third fastener 36 and a screw part 37, which are coupled to the coupling hole 23 of the position adjustment unit 20, are disposed on one end of the rotation member 31.

The guide rail body 32 includes the rail to which the first cage insertion unit 40 is slidably coupled. The rail includes a rail groove 34 and a rail protrusion 33. The first cage insertion unit 40 is slid along the rail groove 34 and is not separated by the rail protrusion 33 until the first cage insertion unit 40 is slid and inserted between the vertebrae.

Preferably, each of the guide rail body 32 and the first cage insertion unit 40 has an arc-type curved shape. Thus, the cage may be inserted through a side surface without incising the rear vertebra due to the arc-type curved shape.

Figure 4A:
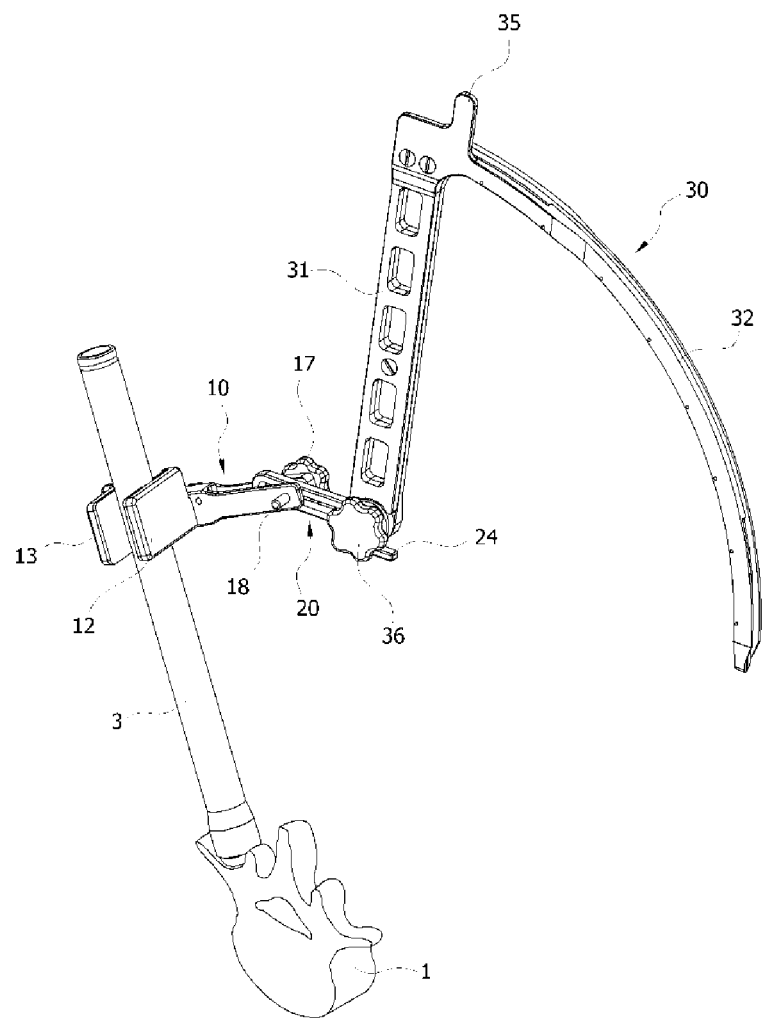
FIG. 4A is a perspective view illustrating a state before the instrument insertion guide constituting the intervertebral body retaining cage insertion device for the minimal invasive surgery is rotated to be inserted between adjacent vertebrae according to the present invention.
Figure 4B:
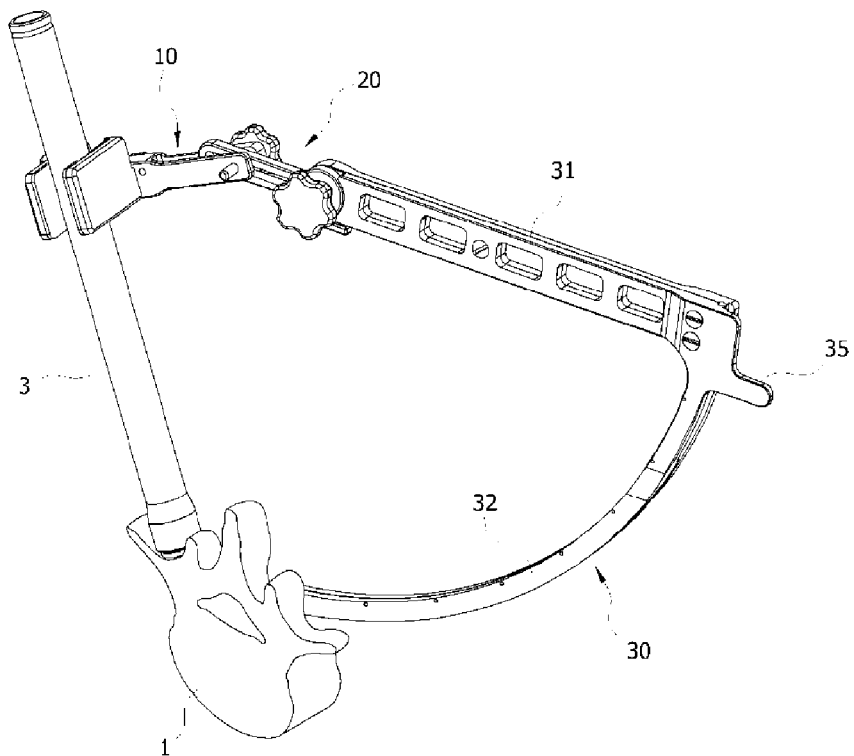
FIG. 4B is a perspective view illustrating a state after the instrument insertion guide constituting the intervertebral body retaining cage insertion device for the minimal invasive surgery is rotated to be inserted between adjacent vertebrae according to the present invention.
Figure 4C:
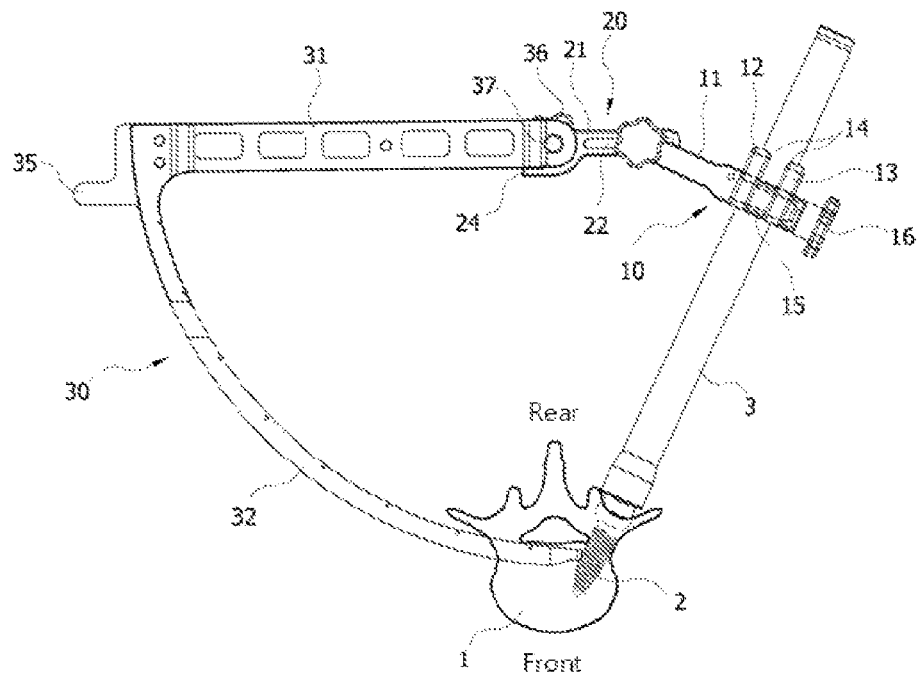
FIG. 4C is a front view illustrating a state after the instrument insertion guide constituting the intervertebral body retaining cage insertion device for the minimal invasive surgery is rotated to be inserted between adjacent vertebrae according to the present invention.

Referring to FIGS. 4A to 4C, a state in which the instrument insertion guide 30 is coupled to the coupling hole 23 of the position adjustment unit 20 to rotate is illustrated. The rotation of the guide rail body 32 is restricted by the rotation prevention protrusion 24 after the guide rail body 32 of the instrument insertion guide 30 is inserted between the vertebrae.

Referring to FIGS. 5A to 7, the first cage insertion unit 40 is moved along the rail provided on the instrument insertion guide 30 to insert the first cage 50 between the adjacent vertebrae.

Particularly, the first cage insertion unit 40 may include a body 42 provided with a rail slidably coupled to the rail provided on the instrument insertion guide 30, a first cage coupling part 43 including two pieces constituted by one side piece and the other side piece on one end of the body 42 and coupled to the first cage 50, a coupling rod 47 that is provided in the body 42, slidable forward and backward, and slid forward and inserted between the one side piece and the other side piece to support the one side piece and the other side piece in directions opposite to each other, and a rod moving member 44 sliding the coupling rod 47 forward and backward, and further include a handle 41 for sliding the first cage insertion unit 40.

When an instrument coupling hole 51 of the first cage 50 and the first cage coupling part 43 are coupled to each other, the rod moving member 44 may be moved forward, and thus, the coupling rod 47 may be moved into the body 42 and inserted between the two pieces constituted by the one side piece and the other side piece, which constitute the first cage coupling part 43. As a result, the one side piece and the other side piece are supported in the directions opposite to each other, and thus, the first cage coupling part 43 that is inserted into and coupled to the instrument coupling hole 51 of the first cage 50 is firmly coupled to the instrument coupling hole 51. A protrusion protruding outward is disposed on each of the one side piece and the other side piece so that the one side piece and the other side piece are more firmly coupled to the instrument coupling hole 51.

When the first cage insertion unit 40 is separated from the first cage 50 after the first cage insertion unit 40 is inserted between the vertebrae to locate the first cage 50 at a fixed position, if the rod moving member 44 is moved backward, the coupling rod 47 may be moved backward, and thus, force supporting the one side piece and the other side piece constituting the first cage coupling part 43 in the directions opposite to each other may be removed. Therefore, the first cage coupling part 43 may be easily separated from the instrument coupling hole 51.

A rail 48 is disposed on the body 42 of the first cage insertion unit 40. The rail 48 is coupled to the rail groove 34 defined in the guide rail body 32 of the instrument insertion guide 30 and then is slid.

Figure 5A:
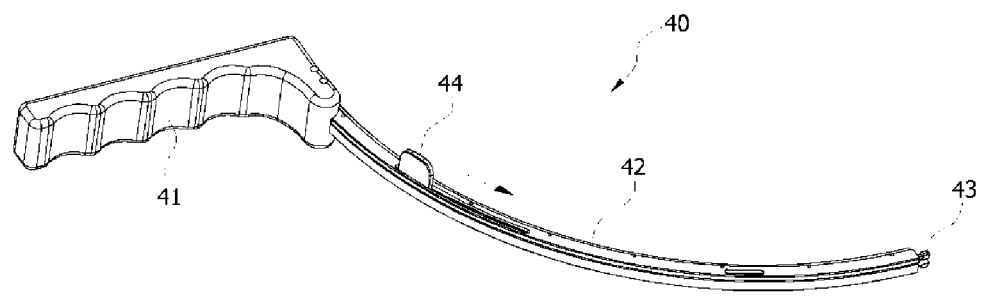
FIG. 5A is a perspective view of a first cage insertion unit.
Figure 5B:
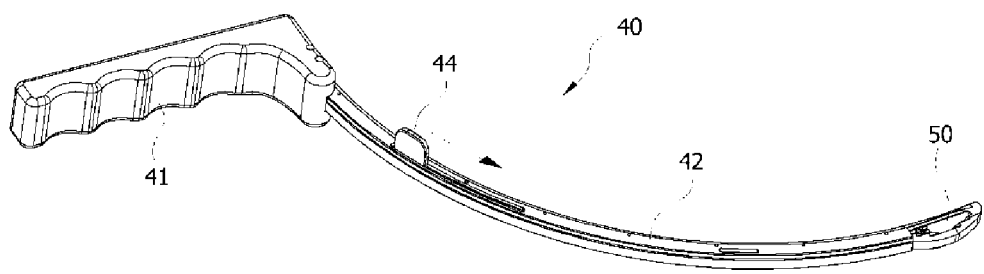
FIG. 5B is a first perspective view illustrating a state in which a first cage is coupled to the first cage insertion unit.
Figure 5C:
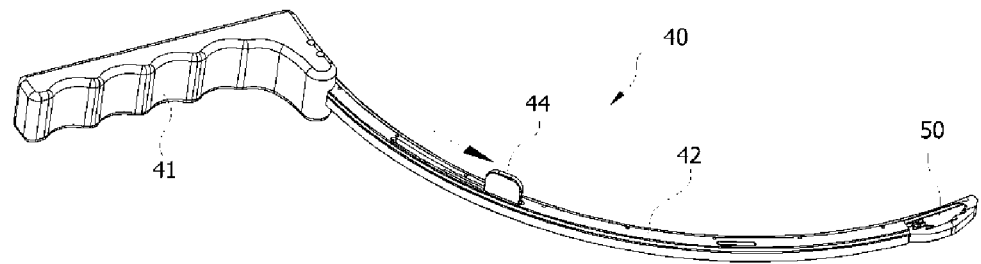
FIG. 5C is a second perspective view illustrating a state in which the first cage is coupled to the first cage insertion unit.
Figure 5D:
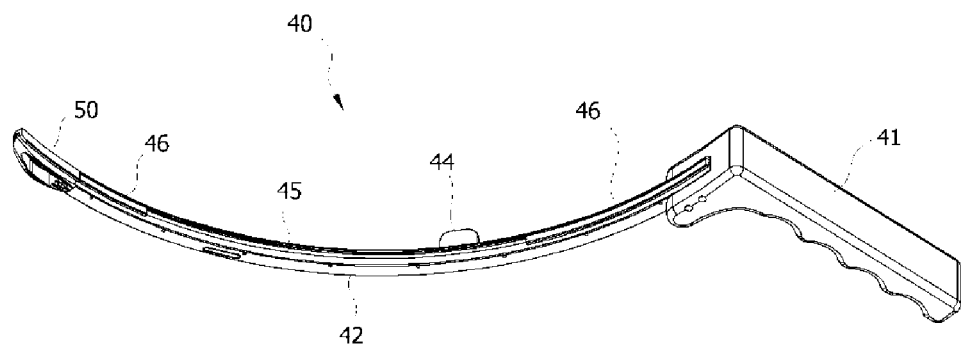
FIG. 5D is a third perspective view illustrating a state in which the first cage is coupled to the first cage insertion unit.
Figure 6:
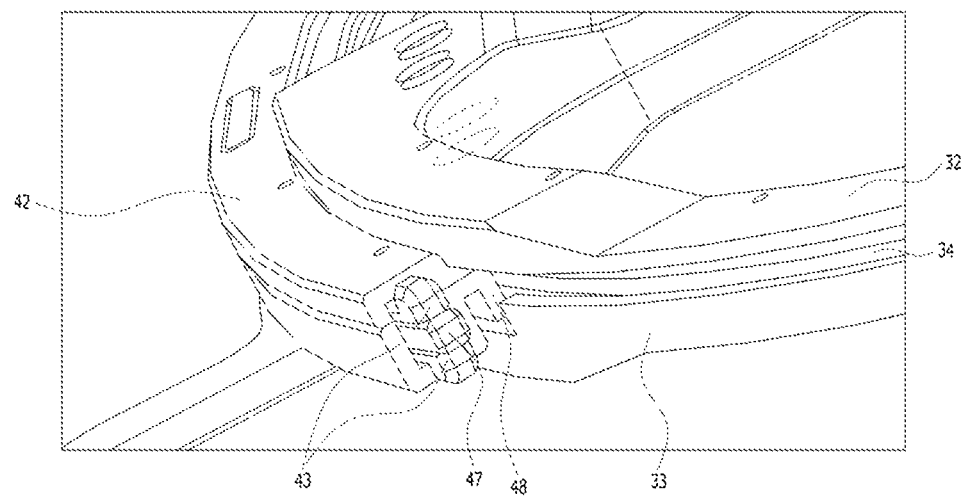
FIG. 6 is a partial enlarged view illustrating a state in which the first cage insertion unit is coupled to a rail of the instrument insertion guide.
Figure 7:
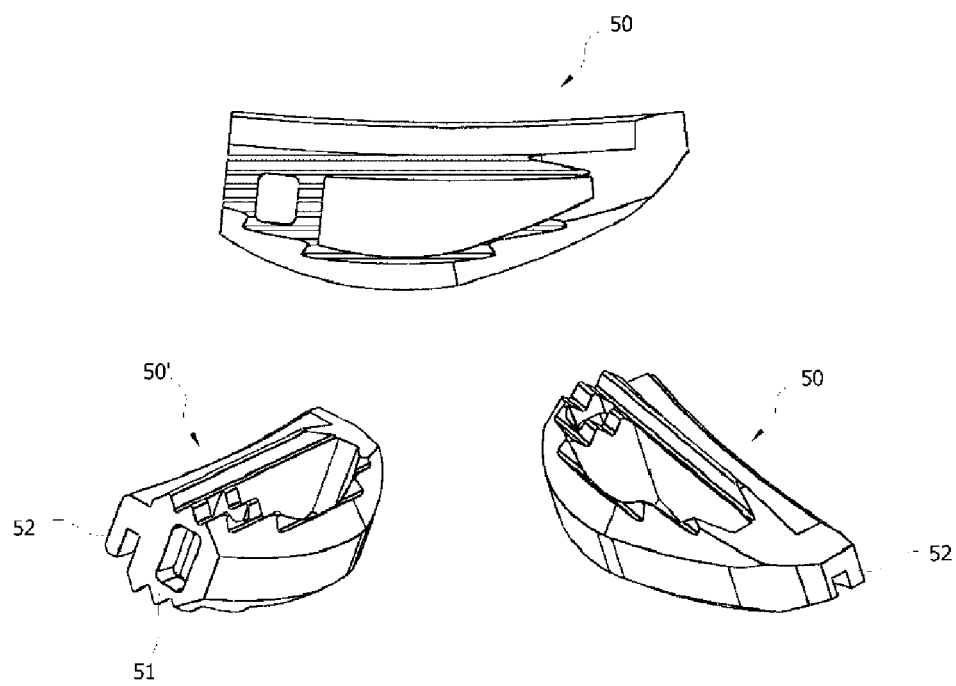
FIG. 7 is front and perspective views of the first cage.
Figure 8:
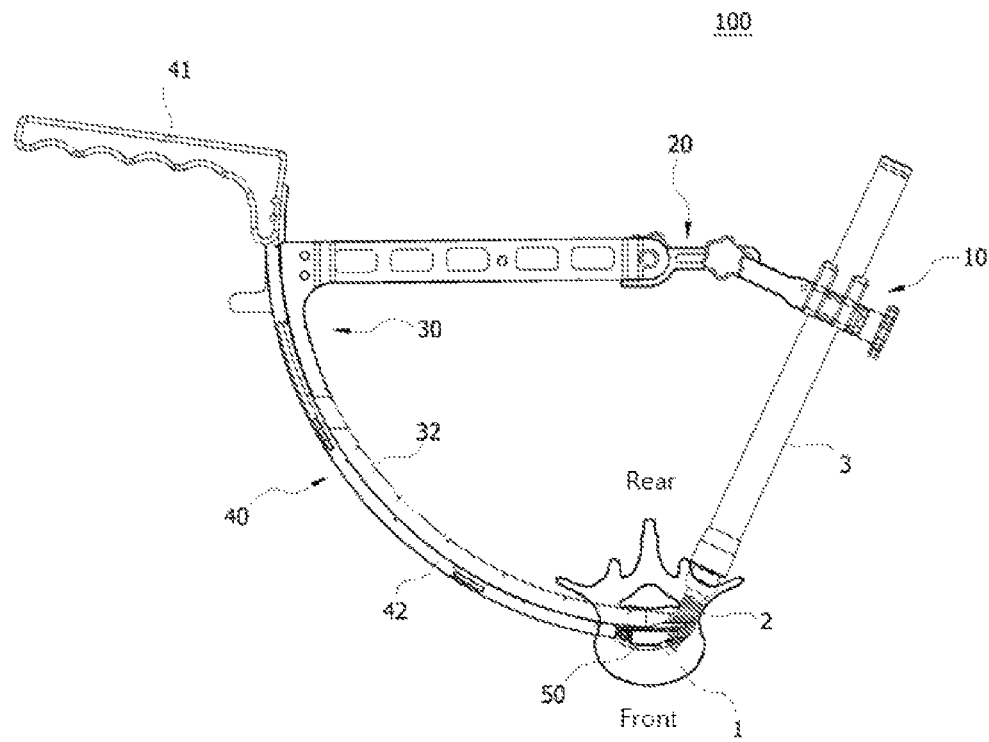
FIG. 8 is a front view illustrating a state in which the first cage insertion unit is slid along the instrument insertion guide and inserted between the vertebrae.
Figure 9:
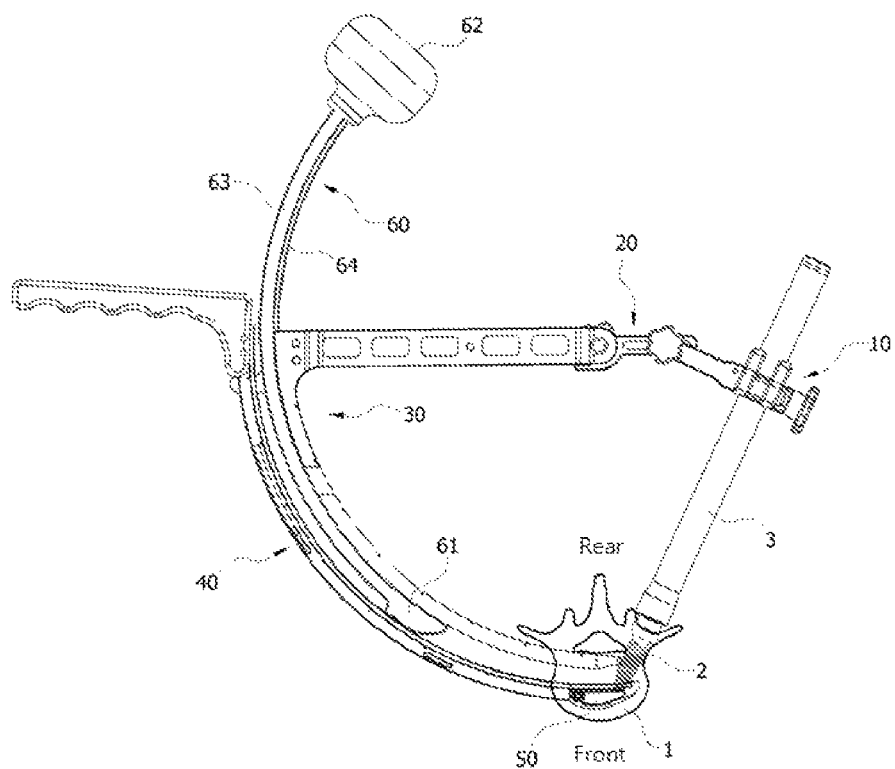
FIG. 9 is a front view illustrating a state in which a spacing unit spaces the first cage insertion unit.
Figure 10:
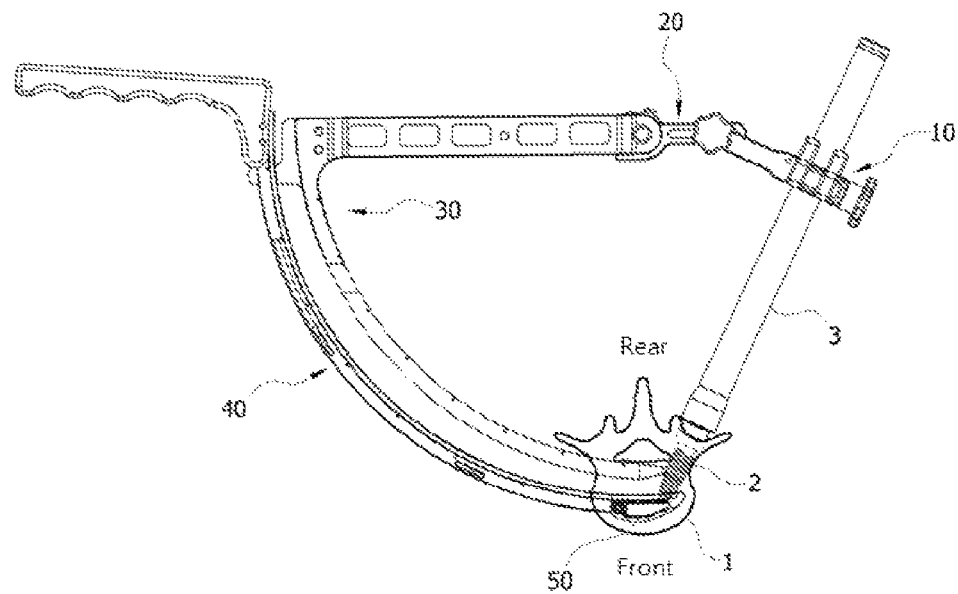
FIG. 10 is a front view illustrating a state in which the first cage insertion unit is spaced by the spacing unit.
Figure 11:
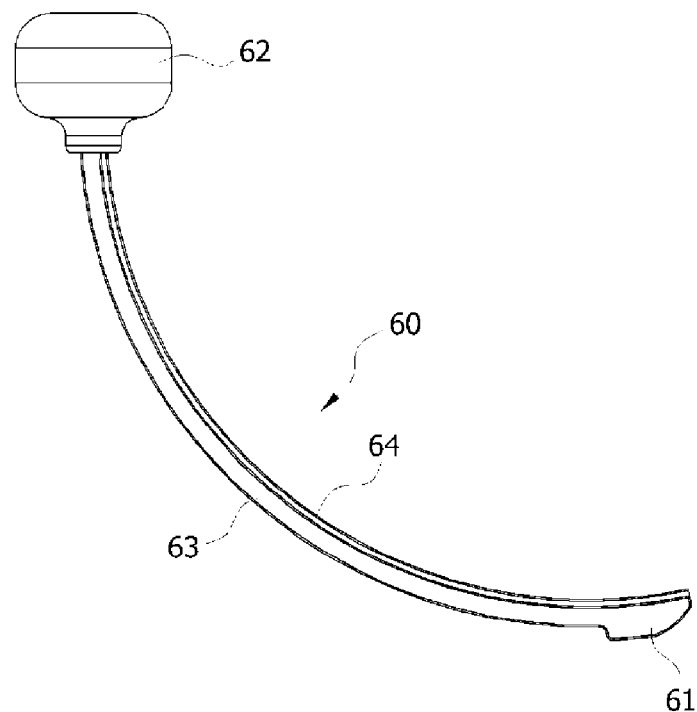
FIG. 11 is a front view of the spacing unit.
Figure 12:
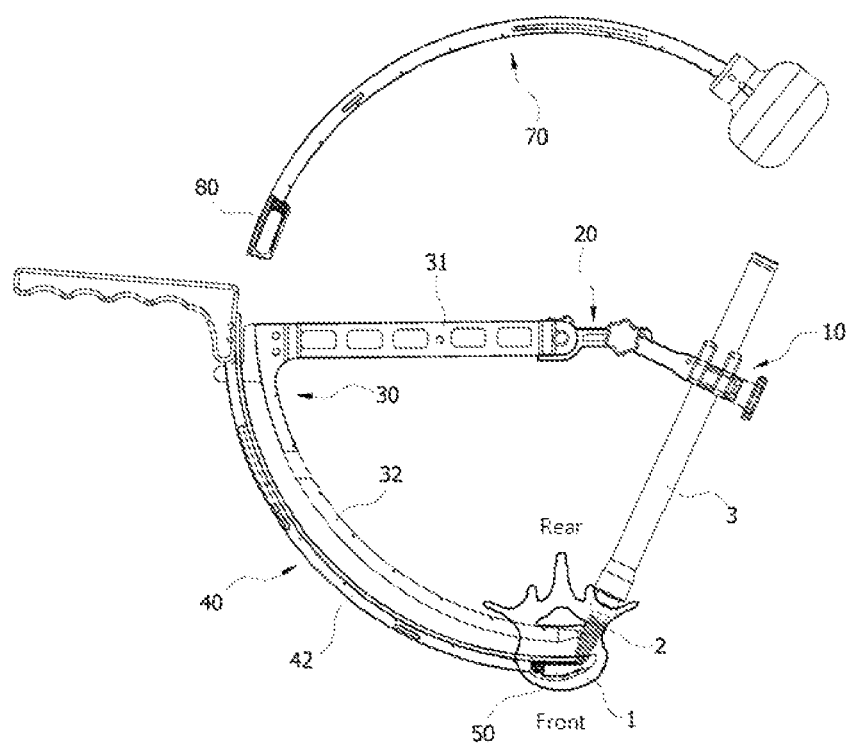
FIG. 12 is a front view illustrating a state in which a second cage insertion unit is inserted into the intervertebral body retaining cage insertion device for the minimal invasive surgery.
Figure 13A:
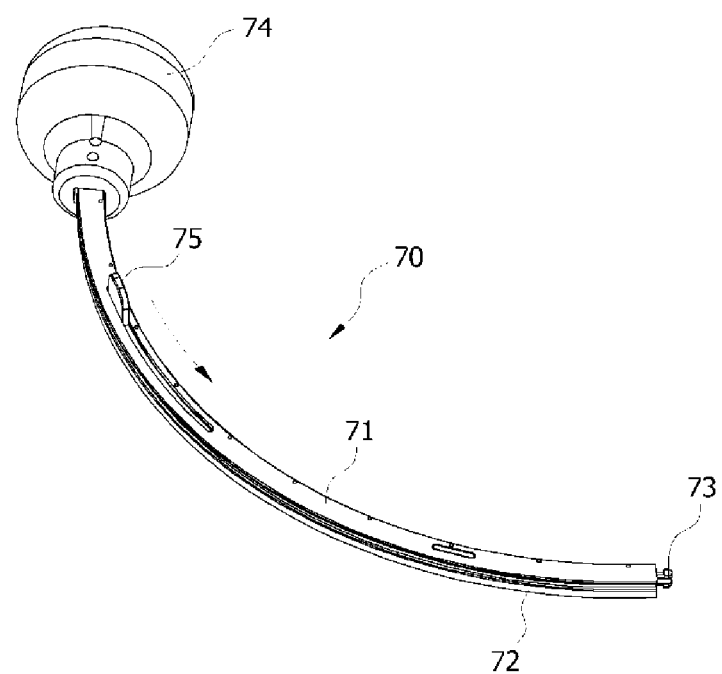
FIG. 13A is a perspective view of the second cage insertion unit.
Figure 13B:
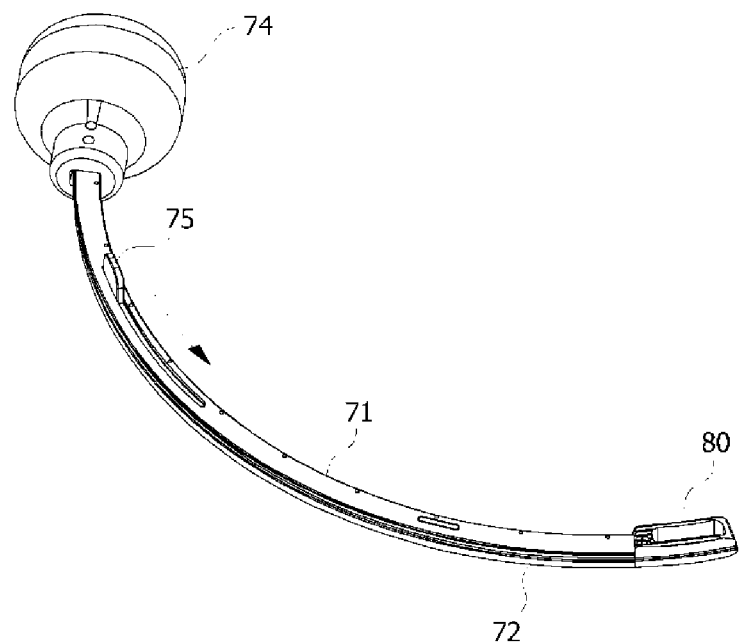
FIG. 13B is a first perspective view illustrating a state in which a second cage is coupled to the second cage insertion unit.
Figure 13C:
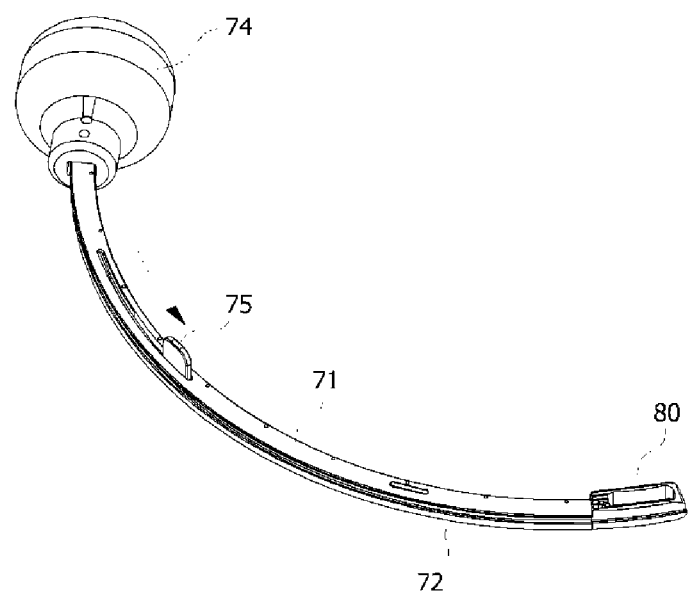
FIG. 13C is a second perspective view illustrating a state in which the second cage is coupled to the second cage insertion unit.
Figure 13D:
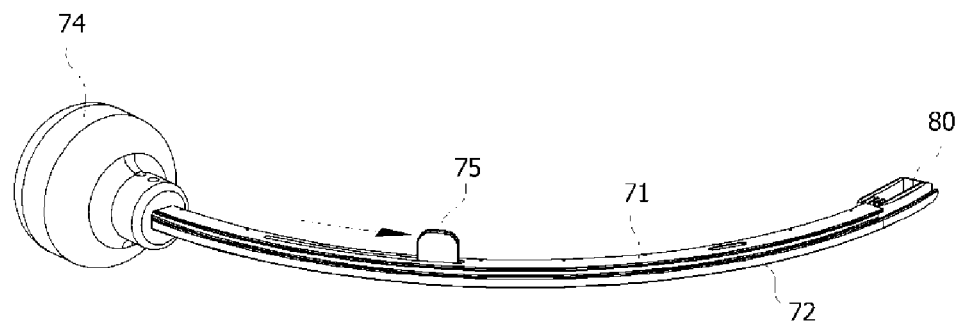
FIG. 13D is a third perspective view illustrating a state in which the first cage is coupled to the first cage insertion unit.
Figure 14:
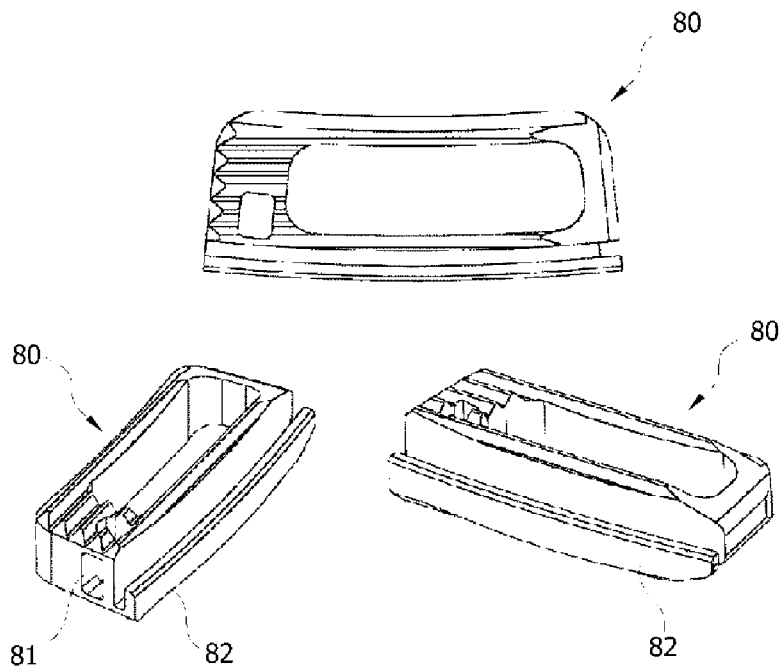
FIG. 14 is front and perspective views of the second cage.

Also, referring to FIG. 5D, a rail groove 45 and a rail protrusion 46 are provided on the body 42 of the first cage insertion unit 40. Since the rail protrusion 46 is disposed in a direction in which the rail protrusion 46 does not overlap the rail protrusion 33 provided on the guide rail body 32 of the instrument insertion guide 30, the rail protrusions may not interfere with each other after the first cage insertion unit 40 is slid along the guide rail body 32 of the instrument insertion guide 30 and inserted between the vertebrae. Thus, the first cage insertion unit 40 may be separated from the instrument insertion guide 30.

Referring to FIGS. 8 to 11, the spacing unit 60 is moved along the rail provided on the instrument insertion guide 30 so as to secure a space for inserting the second cage 80 after the first cage insertion unit 40 is inserted between the adjacent vertebrae, thereby spacing the instrument insertion guide 30 from the first cage insertion unit 40.

Particularly, the spacing unit 60 includes a body 63 provided with a rail 64 slidably coupled to the rail provided on the instrument insertion guide 30 and a head part 61 disposed on one end of the body 63 to push and space the first cage insertion unit 40 from the instrument insertion guide 30 while the body 63 is slid along the rail of the instrument insertion guide 30 and further includes a handle 62.

When the first cage insertion unit 40 is inserted along the rail of the instrument insertion guide 30, although the first cage insertion unit 40 and the guide rail body 32 of the instrument insertion guide 30 are coupled to each other by the rail, the first cage insertion unit 40 may be separated from the instrument insertion guide 30 because the rail protrusions do not interfere with each other.

It is preferable that the head part 61 has a size that is enough to allow the second cage 80 to be inserted and then slid between the instrument insertion guide 30 and the first cage insertion unit 40.

When the spacing unit 60 is moved along the rail provided on the instrument insertion guide 30, the first cage insertion unit 40 is separated from the instrument insertion guide 30. Here, the spacing unit 60 is fully pushed between vertebrae and then moved backward to be withdrawn. As a result, the space for inserting the second cage insertion unit 70 may be secured.

Referring to FIGS. 12 to 15, after the first cage insertion unit 40 is spaced apart from the instrument insertion guide 30 by the spacing unit 60, the second cage insertion unit 70 is moved between the instrument insertion guide 30 and the first cage insertion unit 40 along the rail provided on the first cage insertion unit 40 to insert the second cage 80 between the adjacent vertebrae.

Preferably, each of the spacing unit 60 and the second cage insertion unit 70 has an arc-type curved shape.

Particularly, the second cage insertion unit 70 may include a body 71 provided with a rail 72 slidably coupled to the rail provided on the first cage insertion unit 40, a second cage coupling part 73 including two pieces constituted by one side piece and the other side piece on one end of the body 71 and coupled to the second cage 80, a coupling rod (not shown) that is provided in the body 71, slidable forward and backward, and slid forward and inserted between the one side piece and the other side piece to support the one side piece and the other side piece in directions opposite to each other, and a rod moving member 75 sliding the coupling rod (not shown) forward and backward, and further include a handle 74.

When the instrument coupling hole 81 of the second cage 80 and the second cage coupling part 73 are coupled to each other, the rod moving member 75 may be moved forward, and thus, the coupling rod (not shown) may be moved into the body 71 and inserted between the two pieces constituted by the one side piece and the other side piece, which constitute the second cage coupling part 73. As a result, the one side piece and the other side piece are supported in the directions opposite to each other, and thus, the second cage coupling part 73 that is inserted into and coupled to the instrument coupling hole 81 of the second cage 80 is firmly coupled to the instrument coupling hole 81. A protrusion protruding outward is disposed on each of the one side piece and the other side piece so that the one side piece and the other side piece are more firmly coupled to the instrument coupling hole 81.

When the second cage insertion unit 70 is separated from the second cage 80 after the second cage insertion unit 80 is inserted between the vertebrae to locate the second cage 80 at a fixed position, if the rod moving member 75 is moved backward, the coupling rod (not shown) may be moved backward, and thus, force supporting the one side piece and the other side piece constituting the second cage coupling part 73 in the directions opposite to each other may be removed. Therefore, the second cage coupling part 73 may be easily separated from the instrument coupling hole 81.

Figure 15:
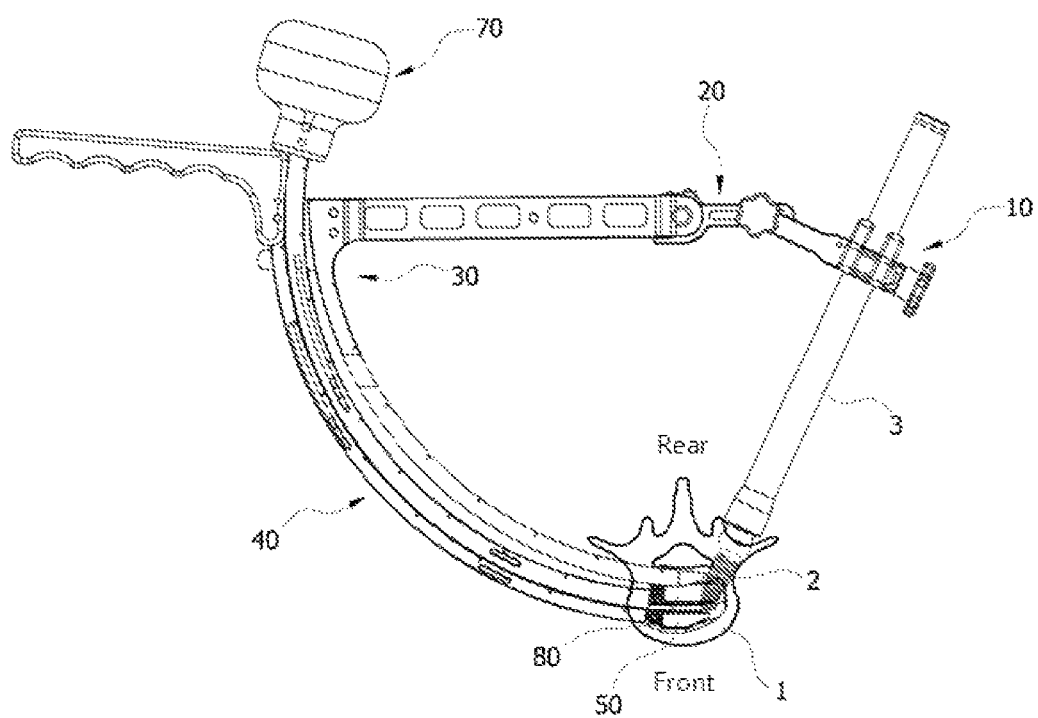
FIG. 15 is a front view illustrating a state in which the second cage insertion unit is slid along the first cage insertion unit and inserted between the adjacent vertebrae.

When the second cage insertion unit 70 is coupled to the rail of the first cage insertion unit 40 and inserted between the vertebrae, a state of FIG. 15 may be realized.

The first cage 50 and the second cage 80 are in contact with each other. Particularly, a coupling part 82 provided on the second cage 80 is slidably coupled to the coupling part 52 provided on the first cage 50, and thus, the first cage 50 and the second cage 80 are stably coupled and disposed without being separated from each other between the vertebrae.

When the rod moving member 75 is moved backward after the second cage 80 is inserted between the vertebrae, the coupling rod (not shown) is moved backward to remove the force supporting the one side piece and the other side piece constituting the second cage coupling part 73 in the directions opposite each other. Therefore, the second cage coupling part 73 may be easily separated from the instrument coupling hole 81. Then, the second cage insertion unit 70 is withdrawn in a direction opposite to that in which the second cage insertion unit 70 is inserted along the rail of the first cage insertion unit 40. After the second cage insertion unit 70 is separated, the first cage insertion unit 70 is separated and withdrawn from the first cage 50 in the same manner. Thus, only the second cage 80 coupled to the first cage 50 may remain between the vertebrae, and the surgical procedure is completed.

According to the present invention, the skin of the back may be slightly incised to conduct the minimal invasive surgery, and also, after the cage is inserted, it may be unnecessary to rotate the cage so that the cage faces the abdomen of the human body.

Also, since the screw driver for inserting the spine-retaining pedicle screw is used as the shaft, it may be unnecessary to provide the separate installation device.

Also, since the bones that are different in position from person to person are adjusted and corrected in position within the device, the cage may be inserted into the accurate position.

Also, since the cage is inserted along the rail having the arc-type curved shape, the cage may be inserted without damaging the neural stems of the spinal nerves.

Also, after the cage is inserted along the rail having the arc-type curved shape, the cage may easily move forward by using the spacing unit. In addition, since the other cage is inserted along the rail having the arc-type curved shape, the two cages may be inserted into the accurate position between the vertebrae, and the cage that is inserted later may be coupled to be engaged with the cage that is inserted first to stably support the vertebrae without separating the two cages from each other.

The present invention is not limited to the foregoing specific preferred embodiment, and also it will be understood by those of ordinary skill in the art that various changes in form and details may be made therein without departing from the spirit and scope of the present invention as defined by the following claims.

The invention claimed is:

1. An intervertebral body retaining cage insertion device for a minimal invasive surgery, which inserts a cage between adjacent vertebrae by using a screw driver for inserting a spine-retaining pedicle screw as a shaft, the intervertebral body retaining cage insertion device comprising:
   a retaining unit detachably coupled to a predetermined position on the screw driver;
   a position adjustment unit having a hole defined along a longitudinal direction of a body, wherein the retaining unit is fixed and coupled to a predetermined position of the hole;
   an instrument insertion guide rotatably coupled to an end of the position adjustment unit and inserted between the adjacent vertebrae; and
   a first cage insertion unit configured to be moved along a rail provided on the instrument insertion guide to insert a first cage between the adjacent vertebrae.

2. The intervertebral body retaining cage insertion device of claim 1, wherein the retaining unit comprises:
   a body;
   a first pressing/retaining plate disposed on one side of the body;
   a second pressing/retaining plate disposed to face the first pressing/retaining plate and configured to be moved to the first pressing/retaining plate to press the screw driver;
   a transfer screw moving the second pressing/retaining plate forward and backward;
   a first fastener rotating the transfer screw; and
   a second fastener fixed and coupled to the predetermined position of the hole defined in the position adjustment unit.

3. The intervertebral body retaining cage insertion device of claim 1, wherein the position adjustment unit has a guide hole defined along the longitudinal direction of the body and a coupling hole to which the instrument insertion guide is coupled and comprises a rotation prevention protrusion preventing the instrument insertion guide from being rotated after the instrument insertion guide coupled to the coupling hole is rotated to be inserted between the adjacent vertebrae.

4. The intervertebral body retaining cage insertion device of claim 1, wherein the instrument insertion guide comprises:
   a rotation member having one end coupled to the position adjustment unit; and
   a guide rail body disposed on the other end of the rotation member and provided with a rail to which the first cage insertion unit is slidably coupled.

5. The intervertebral body retaining cage insertion device of claim 4, wherein each of the guide rail body and the first cage insertion unit has an arc-type curved shape.

6. The intervertebral body retaining cage insertion device of claim 1, wherein the first cage insertion unit comprises:
   a body provided with a rail slidably coupled to the rail provided on the instrument insertion guide;
   a first cage coupling part comprising two pieces constituted by one side piece and the other side piece on one end of the body and coupled to the first cage;
   a coupling rod provided in the body, slidable forward and backward, and slid forward and inserted between the one side piece and the other side piece to support the one side piece and the other side piece in directions opposite to each other; and
a rod moving member sliding the coupling rod forward and backward.

7. The intervertebral body retaining cage insertion device of claim 1, further comprising a spacing unit moved along the rail provided on the instrument insertion guide to space the instrument insertion guide from the first cage insertion unit so as to secure a space for inserting a second cage after the first cage insertion unit is inserted between the adjacent vertebrae.

8. The intervertebral body retaining cage insertion device of claim 7, wherein the spacing unit comprises:
a body provided with a rail slidably coupled to the rail provided on the instrument insertion guide; and
a head part disposed on one end of the body to push and space the first cage insertion unit from the instrument insertion guide while the body is slid along the rail of the instrument insertion guide.

9. The intervertebral body retaining cage insertion device of claim 7, further comprising a second cage insertion unit configured to be moved between the instrument insertion guide and the first cage insertion unit along a rail provided on the first cage insertion unit to insert the second cage into the adjacent vertebrae after the first cage insertion unit is spaced apart from the instrument insertion guide by the spacing unit.

10. The intervertebral body retaining cage insertion device of claim 9, wherein each of the spacing unit and the second cage insertion unit has an arc-type curved shape.

11. The intervertebral body retaining cage insertion device of claim 9, wherein the second cage insertion unit comprises:
a body provided with a rail slidably coupled to the rail provided on the first cage insertion unit;
a second cage coupling part comprising two pieces constituted by one side piece and the other side piece on one end of the body and coupled to the second cage;
a coupling rod provided in the body, slidable forward and backward, and slid forward and inserted between the one side piece and the other side piece to support the one side piece and the other side piece in directions opposite to each other; and
a rod moving member sliding the coupling rod forward and backward.

* * * * *